United States Patent

Sovak et al.

[11] Patent Number: 6,072,069
[45] Date of Patent: Jun. 6, 2000

[54] BIODEGRADABLE NONIONIC CONTRAST MEDIA

[75] Inventors: Milos Sovak, La Jolla; Allen L. Seligson, San Marcos; James Gordon Douglass, III, San Diego, all of Calif.

[73] Assignee: Biophysica, Inc., La Jolla, Calif.

[21] Appl. No.: 09/186,872

[22] Filed: Nov. 4, 1998

[51] Int. Cl.$^7$ .................. C07C 271/48; C07C 69/96; A01N 49/04

[52] U.S. Cl. .................. 558/266; 560/132; 564/153; 564/158; 424/9.45; 424/9.453; 424/9.454; 424/9.455

[58] Field of Search .................. 558/266; 560/132; 564/153, 158; 424/9.45, 9.453, 9.454, 9.455

[56] References Cited

U.S. PATENT DOCUMENTS 4,278,654  7/1981  Rakli .

OTHER PUBLICATIONS

Kalsch et al. (1999) *Science of the Total Environment* 225: 143–153.
Kummerer et al. (1998) *Chemosphere* 36: 11: 2437–2445.
Rode et al. (Aug. 1998) *Applied & Environmental Microbiology* 64:8:3114–3117.
Steger–Hartmann, et al. (1999) *Ecotoxicology and Environmental Safety* 42:274–281.

*Primary Examiner*—Fiona T. Powers
*Attorney, Agent, or Firm*—Bertram I. Rowland; Rae-Venter Law Group, P.C.

[57] ABSTRACT

Novel non-ionic contrast media are provided, which fulfill the requirements for x-ray visualization media, while being biodegradable. The compounds are characterized by being triiodo-3,5-diaminobenzoic acid derivatives, where the functional groups are derivatized with hydroxyalkyl groups and the amino functionalities are further derivatized with acyl substituents of one carbon acids. Also, triiodophloroglucinol oxyalkyl substituted derivatives are provided.

15 Claims, No Drawings

BIODEGRADABLE NONIONIC CONTRAST MEDIA

TECHNICAL FIELD

The field of this invention is novel environmentally degradable non-ionic radiographic contrast media, which have good stability in vivo.

BACKGROUND

Current radiographic contrast media ("CM") are derivatives of triiodobenzene. Whether ionic or non-ionic, monomeric or dimeric, they are required to be stable compounds for their function. The in vivo stability is very desirable for an injectable diagnostic composition which should be excreted from the body unchanged. An ideal CM should then degrade in the environment into naturally recyclable components. With the current CM, even after very extended periods in sewage treatment plants, in ground water and in the oceans, the aromatic iodine remains firmly bound in these intact molecules. The approximately 3000 tons which are annually employed clinically, are quantitatively disposed of in the environment, where they increasingly accumulate. There is a growing concern about the potiential environmental impact of these "immutable" substances.

It has been previously suggested to collect and recycle CM, but the logistics, handling and the safety issues face insurmountable obstacles. It is therefore desirable to develop alternatives, such as contrast materials which have the desired in vivo properties, e.g. good stability and biological tolerance in the host, and which would when disposed of into the environment, be degraded.

Such compounds would have to fulfill the manifold requirements of the CM employed today. They would have to be economically feasible, having a simple synthetic procedure and inexpensive starting materials and reagents. They should be stable to autoclaving to provide a sterile CM. However, contrary to todays CM, following exposure to the environment and bacterial attack, the new CM would lose iodine and be degraded to benign products.

It is common knowledge that the triiodo-derivatives of 5-acylamidoisophthalic acid, such as the commercially available Iohexol, Iopamidol, Ioversol, Iodixanol, Iotrolan and Ioxilan are all extremely stable and upon UV irradiation in water or residence in sewage or soil, do not lose the iodine over extended periods. The same is true for the triiodo-3,5-diaminobenzoic acid, known as diatrizoate. All these compounds share acetyl acyl substituents, except Iopamidol, where the acyl substituent is lactoyl. Formyl has been avoided because of its assumed instability. However, novel stable CM employing formyl acyl subsituents have been previously disclosed, where appropriate N-alkylation of triiodoisophthalic formylamide products were found to be stable, but the product has not yet found commercial acceptance.

SUMMARY OF THE INVENTION

Biodegradable non-ionic contrast media are provided which are aryltriiodo compounds, being diaminobenzoyl derivatives or phloroglucinols, wherein the nitrogens and oxygens are directly or indirectly substituted with hydroxyalkyl groups. The subject compounds fulfill the requirements for non-ionic contrast media while being degraded in conventional sewage treatment facilities.

DESCRIPTION OF THE SPECIFIC EMBODIMENTS

In accordance with the subject invention, novel non-ionic contrast media are provided, which are stable, biodegradable aryltriiodo compounds. The compounds are derivatives of triiodobenzoic acids or triiodophenols with substituted amino or oxy groups at the 3- and 5-positions, where the substituents are usually symmetrical. The amino groups are both substituted with one carbon atom acyl groups, where the carbonyl is bonded to other than carbon atoms, e.g. H, O or N, particularly formyl groups, with the amino groups preferably being further substituted, having alkyl or oxyalkyl, particularly hydroxyalkyl, substituents bonded directly to the nitrogen atom. When the carbonyl is bonded to a heteroatom, a carbonate (oxycarbonyl) or carbamyl (aminocarbonyl) group forming a carbamate or urea functionality results. The oxyalkyl groups have from 2–10 carbon atoms, usually 2–8 carbon atoms and at least one hydroxyl group and up to n-1 hydroxyl groups at other than the α-position, where n is the number of carbon atoms. The molecule, when monomeric, will generally have a total of not more than about 32 carbon atoms, usually not more than about 24 carbon atoms, and not more than about 20 hydroxyl groups, usually not more than about 18 hydroxyl groups, more usually not more than about 12 hydroxyl groups. The dimeric molecule may have twice as many carbon atoms and hydroxyl groups, generally having about 10% fewer total carbon atoms and hydroxyl groups. Preferably, the alkyl groups will be from about 2–6 carbon atoms, frequently 2–4 carbon atoms, and have from 1–5, usually 1–3 hydroxyl groups, at other than the α-position. There will normally be at least 2 oxyalkyl groups for each aromatic ring and not more than 6, usually not more than 5, frequently not more than 4, oxyalkyl groups.

The subject compounds will for the most part come within the following formula:

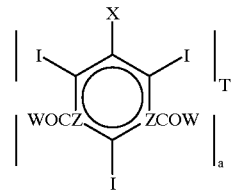

wherein
a is 1 or 2,
when a is 1, T is OH, or Z-R, usually Z-alkyl of from 1 to 10, usually 1 to 6, more usually 1 to 3, carbon atoms, e.g. methyl, Z-oxyalkyl, particularly hydroxyalkyl, of from 2 to 10, usually 2 to 6, more usually 2 to 4 carbon atoms and 1 to n-1 oxy groups or alkyl of from 1 to 10, usually 1 to 6, more usually 1 to 4 carbon atoms, particularly methyl and ethyl, where any oxy group is at other than the α-carbon atom, where the alkyl groups may be straight chain or branched, usually straight chain;
when a is 2, T is a bridging group, a bis-α,ω-diaminohydroxyalkylene of from 2 to 10, usually 2 to 6, more usually 2 to 4 carbon atoms and from 0 to n-2 oxy, particularly hydroxyl, groups at other than the α-carbon atom, where the alkylene may be straight chain or branched, usually straight chain;

X is OCO or C=O;

Z is NR or O;

W is H, OR, or $NR_2$;

wherein all of the Rs are the same or different, usually H, alkyl or hydroxyalkyl of from 1 to 10, usually 1 to 8, more usually 1 to 6 carbon atoms, particularly 1 to 4 carbon atoms, where hydroxyalkyl groups will have at least 2 carbon atoms.

(For each of the ranges, each number in the range is to be considered to be set forth individually, as if it had been set forth specifically.)

Groups bonded to the annular carbon atom include OR, OCOR, OCNHR, $OCNR_2$, NR(COR), N(CHO)R, $NH(CO_2R)$, NH(CONHR), $NH(CONR_2)$, NR(CONHR), and $NR(CONR_2)$, where at least one R in each of the functional groups is an oxyalkyl, particularly an hydroxyalkyl. That is, there will be at least one oxyalkyl group bonded directly or indirectly to each heteroatom bonded to an annular carbon atom. For the most part the oxy groups will be of from 0 to 3 carbon atoms, being hydroxyl, methoxy, ethoxy and propoxy, usually hydroxyl.

Included in the genus is a subgenus of particular interest having the following formula:

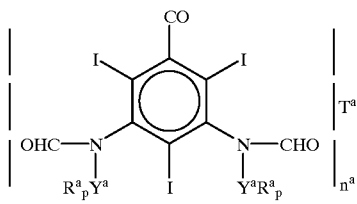

wherein:

$T^a$ and $n^a$ come within the definitions of T and n, respectively;

the $R^a$s may be the same or different, where $R^a$ is H or comes within the definition of R, when bonded to nitrogen, and R when bonded to oxygen, but are usually H or of from 1 to 6 carbon atoms, more usually of from 2 to 5 carbon atoms and from 0 to n-1 oxy, particularly, hydroxyl groups, usually of from 1 to n-1 hydroxyl groups, any hydroxyl groups being at other than the α-carbon atoms, there being at least one oxyalkyl group bonded directly or indirectly to the amino group bonded to the annular carbon atom;

p is when when R is bonded to oxygen and 2 when R is bonded to nitrogen, and the two $Y^a$s may be same or different, normally the same, and are a bond, carbonyl, oxycarbonyl (carbonate) or aminocarbonyl (carbamate), where the oxycarbonyl defines a urethane and the aminocarbonyl defines a urea, preferably $Y^a$ is a bond.

Usually where an R group is bonded to nitrogen other than the annular carbon substituted nitrogen, one of the R groups will be hydrogen.

Another group of compounds is based on phloroglucinol, where the compounds would come within the following formula:

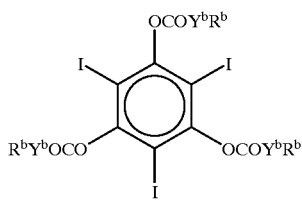

wherein:

the $R^b$s and the $Y^b$s are the same or different, normally the same, and $R^b$ and $Y^b$ come within the definitions of R and Y, respectively.

Illustrative alkyl groups include methyl, ethyl, propyl, 2-hydroxyethyl, 2,3-dihydroxyethyl, 2,3,4-trihydroxybutyl, 1,3,4-trihydroxybutyl, 1-deoxymannitol, 1-deoxyglucitol, etc.; illustrative alkylene groups include ethylene, 2-hydroxyl-1,3-propylene, 2,3-dihdroxy-1,4-butylene, etc.

For the most part the nitrogens will have at least one hydroxyalkyl group. Preferably the symmetrically situated groups bonded to the nitrogen atoms bonded to an annular atom will be the same, so that a symmetrical molecule is obtained having an axis of symmetry along carbon atoms 1 and 4 of the ring. Similarly, the phloroglucinol derivatives will be symmetrical, that is, the substituents on the oxygen atoms will all be the same.

The subject compounds may be prepared in accordance with conventional ways. The triiodobenzoic acid is reacted with an active form of an organic acid, e.g. mixed anhydride, while cooling, followed by activation of the benzoic acid carboxyl group. The benzoic acid carboxyl group may be activated by forming the acyl chloride, mixed anhydride, carbodiimide derivative, etc. The resulting activated acyl compound is then combined with the appropriate amine in the presence of an acid acceptor in a polar solvent. The nitrogen atoms bonded to an annular atom may then be further derivatized by reaction with an activated halide or pseudohalide under mildly basic conditions, or with a precursor to a carbonate or carbamate linker. Hydroxyl groups may be appropriately protected with readily removable acyl groups or as ketonides. At each stage the product may be isolated and purified in accordance with conventional ways, e.g. chromatography, ion exchange chromatography, extraction, precipitation, etc.

The phloroglucinol compounds may be prepared by combining the appropriate solketal chloroformate with the triiodophloroglucinol and a tert.-amine in a polar solvent at low temperatures, e.g. liquid nitrogen. The ketonide may be hydrolysed by trifluoroacetic acid in a polar solvent comprising an alkanol at moderate temperatures. The 3,5-dicarbamoyloxy derivatives of triiodobenzamides can be prepared using the procedures described for the other compounds of this invention.

All of the subject compounds will be mixtures of various stereoisomers, due to the enantiomers at the various substituted side groups and the steric hindrance resulting from the iodines to rotation of the groups bonded to the aromatic annular carbon atoms. The complex mixtures that result enhance the water solubility of the product to allow for high levels of iodine in the formulations. Thus, one could have optically active products, meso forms and racemic mixtures.

For an acceptable non-ionic contrast medium, the compound must have high water solubility, substantially miscible with water, acceptable stability at elevated temperatures, particularly as formulated when sterilized in an autoclave, low toxicity, low osmolality, and low viscosity. The compounds should have an economic process for their production and should produce a minimum of side products, so that during the preparation of the intermediates and final products, particularly the final product, interfering side products should be minimally produced and be capable of ready removal.

The water solubility of the compounds should permit at least about 270 mg I/ml. The osmolality of the compounds should not exceed about 800 mOs/kg at 300 mg I/ml. The viscosity should be not more than about 9 cP at 37° C. at 300 mg I/ml. The compounds should be stable to autoclaving at 120° C. for 20 min. The compounds should have low toxicity, generally having in mice an i.v. $LD_{50}$ greater than about 15 g I/kg. Desirably, the intracerebral $LD_{50}$ is at least 1.5 g I/kg in mice.

The subject compounds are soluble in water at room and elevated temperatures, as required for a non-ionic contrast medium. The subject compounds are found to have good in vitro stability. The compounds are stable for extended periods of time at elevated temperatures, particularly at least 38° C., desirably at least about 1 h, usually 2 h in human serum and even at higher temperatures for sterilization, provided that the pH is reduced, albeit transiently to a pH in the range of 4–6, more usually 4.5–5.5. The subject compounds provide for the desired osmolality and viscosity associated with non-ionic contrast media.

The subject compounds may be readily formulated for use in a buffer comprising Trizma [tris(hydroxymethyl) aminomethane] in the range of about 0.1 to 5 mM and EDTA in the range of about 0.1 to 0.5 mM at a concentration of the subject compounds at about 100 to 500 mgI/ml. This formulation is convenient for sterilization of the subject compounds.

The subject compounds find use for medical imaging in a wide variety of situations, such as urography, angiography, myelography, contrast enhancement of blood pool in computerized tomography and for visualization of body cavities. The subject compounds are administered as a sterile aqueous solution in accordance with conventional ways and the particular body compartment which is to be visualized.

The subject compounds are degraded in the environment, particularly by bacterial action, light degradation and combinations thereof. The subject compounds are degraded in sewage systems, e.g. activated sludge, in soil, water, other disposal systems and the like.

The following examples are offered by way of illustration and not by way of limitation.

EXPERIMENTAL

The title compounds were subjected to preliminary stability testing by exposure to a phosphate buffer at pH 7.3, 37° and/or 100° C., and for selected compounds, also by stability testing in the human serum at 38° C. The percent of the remaining test compound as a function of time after incubation was determined by HPLC (Table 1).

TABLE 1

| | Stability of Biodegradable CM | | | | | | | |
|---|---|---|---|---|---|---|---|---|
| Compound | Solvents | 0.6 hrs. | 1.2 hrs. | 3 hrs. | 6 hrs. | 24 hrs. | 94 hrs. | 720 hrs. |
| BP-377 | $KH_2PO_4$ at 38° C. | 100 | — | — | — | 99 | | |
| BP-377 | $KH_2PO_4$ at 100° C. | — | — | 4.8 | 1.9 | 0.3 | | |
| BP-419 | $KH_2PO_4$ at 38° C. | — | 11.5 | 0.4 | | | | |
| BP-508 | $KH_2PO_4$ at 100° C. | 100 | — | 97.2 | — | 80.1 | 75.3 | |
| BP-508 | Human serum at 38° C. | 100 | — | 100 | — | 100 | — | 98.6 |
| BP-755 | $KH_2PO_4$ at 100° C. | 100 | — | — | 99.1 | 98.5 | 96.4 | |
| BP-755 | Human serum at 38° C. | 100 | — | — | 100 | 100 | 99.7 | |

Very surprisingly BP-508 and BP-755 at 100° C. had shown a steady deterioration with time while the same compounds in human serum did not change. When BP-508 and BP-755 were separately incubated with phosphate buffer at 100° C. for 10 days, or 12 weeks in a wet sewage derived humus, thereafter extracted, and degradation products isolated by HPLC, evidence of a loss of aromatic iodine was provided by $^1$H-NMR analysis. NMR displayed one new resonance for Ar-H in the aromatic and formyl regions.

BP-508 and BP-755, which are preferred products, consist of four isomers, which were isolated by HPLC. The endo/exo isomers are interconvertible, while the cis/trans were not, but all, nevertheless, were found to be water soluble. Concentrated solutions seeded with crystals indicate stability of super-saturated solutions. BP-508 has at 300 mg I/mL an osmolality of approximately 530 mOsm/kg and viscosity of 5.4 cps. BP-755 has an osmolality of 545 mOsm/kg. Solutions of 300 mg I/mL of BP-508 and BP-755 were subject to sterilization by autoclaving at 120° C. for 20 minutes. When pH 7.4 phosphate buffer was used, the compounds showed by HPLC some decomposition, but when formulated with Trizma (Tris) and EDTA, there was no decomposition, except that a new minor impurity (>0.05%) was observed resulting from dealkylation. Use of Tris, which at higher temperatures lowers pH, has been previously reported for contrast media, but not claimed for the formyl-containing species (U.S. Pat. No. 4,278,654, Rakli, Jul. 14, 1981).

The systemic toxicity of the subject compounds was addressed by standard "up and down" i,v, LD50 method. Sterile solution of 300 mg I/mL was injected at the rate of 1 mL/min; the approximate LD50 is 14–16 g I/kg bw.

In 5 rats injected i.v. daily, 8 times, with 3.75 g I/kg bw, there was no hematuria or anuria and all rats survived.

Example 1

3,5-diformylamido-2,4,6-triiodo-benzoic acid chloride

To 3,5,diamino-2,4,6-triiodbenzoic acid (80 g) in formic acid (400 mL, 95–98%) at 0° C. was added isobutyric anhydride (250 mL) over 1 h, stirred at RT for 10 h and filtered. The solid was washed with ethyl acetate (5×100 mL), dried, and treated with activated charcoal to yield 70.5 g (80%).

To 50 g of the product in ethyl acetate (300 mL) at 75° was added thionyl chloride (25 mL), stirred for 14 h and evaporated. The solid was washed with ethyl acetate, filtered and dried to yield 43.7 g (85%).

Example 2

3,5-diformylamido-2,4,6-triiodo-N-methyl-D-glucabenzamide (BP-377)

To a solution of N-methyl-D-glucamine (3.88 g) and triethylamine (2.77 mL) in 2-methoxyethanol (50 mL) was added 3,5-diformylamido-2,4,6-triiodobenzoic acid chloride (10 g). After stirring at RT for 5 h, and evaporation, the residue was dissolved in methanol (50 mL) and added to stirred isopropanol (250 mL). The white precipitate was filtered, dissolved in $H_2O$ (30 mL), treated with ion exchange resin and activated charcoal, to yield 7.9 g (63%) (BP-377).

Example 3

3,5-N,N'-bis(2,3-dihydroxypropyl)formylamido-2,4,6-triiodo-N"-(2,3-dihydroxypropyl) benzamide (BP-508)

To a solution of 3-amino-1,2-propanediol (6.5 mL) and triethylamine (15.9 mL) in DMA (50 mL) was added 3,5-diformylamido-2,4,6,-triiodobenzoic acid chloride (45.8 g). After stirring at RT for 3 h, evaporation gave an oil and a white solid, which precipitated by $H_2O$ (500 mL) yielding 48.4 g (97%) 3,5-diformylamido-2,4,6-N-(2,3-dihydroxypropyl) benzamide.

To a suspension of trisodiumphosphate dodecahydrate (144 g) in 2-methoxyethanol (200 mL) was added 3-chloro-1,2-propanediol (25.5 mL) over 40 min and the mixture stirred at room temperature for 1 h. 3,5-diformylamido-2,4,6-N-(2',3'-dihydroxypropyl) benzamide (50 g) was added over 10 min. After stirring for 72 h at RT, filtration and acidification to pH 2–3 with concentrated hydrochloric acid, the solution was neutralized with 25% sodium methoxide in methanol to pH 5–6 and evaporated to an oil. $H_2O$ (200 mL) was added and the solution treated with ion exchange resin and activated charcoal. After evaporation and addition of methanol (200 mL), the solution was added to stirred isopropanol (1 L). A white precipitate was isolated by filtration and dried to yield 32.6 g (53%) 3,5-N,N'-bis-(2', 3'-dihydroxypropyl) formylamido-2,4,6-triiodo-N"-(2",3"-dihydroxypropyl) benzamide (BP-508).

Example 4

2,4,6-triiodo-1,3,5-tri(2',3'-dihydroxypropyl) carbonato benzene BP-419)

Solketal chloroformate (4.44 mL) was added dropwise to a stirred solution of 2,4,6-triiodophloroglucinol (5.0 g) and pyridine (2.22 mL) in THF (50 mL) at −78° C. under $N_2$, stirred for 1 h, warmed to RT and filtered. Solids were washed with THF (1×20 mL) and the filtrate evaporated to a yellow solid, which was purified by silica gel chromatography (9/1, dichloromethane/acetone) to yield 5.7 g (57%) 2,4,6-triiodo-1,3,5-trisolketalcarbonatobenzene.

Trifluoroacetic acid (1.7 mL) was added to 2,4,6-triiodo-1,3,5-trisolketal carbonatobenzene (4.0 g) in methanol (40 mL) and acetonitrile (20 mL). The reaction was followed by TLC (80/20 $CHCl_3$/methanol), evaporation yielded 3.5 g (>99%) of the title compound.

Example 5

Formulation and sterilization of BP-508

To BP-508 (1.277 g) was added Trizma [tris (hydroxymethl)aminomethane (2.4 mg)] $CaNa_2$ EDTA (0.2 mg) and double distilled water to a volume of 2 mL. The solution, which contained 300 mg I/mL, was ultrafiltered into a sterile 2 mL vial, which was autoclaved at 120° C. for 20 minutes and cooled to RT.

Example 6.

3,5-N,N-bis(2',3',4'-trihydroxybutyl) formylamido-2,4,6-triiodo-N"-(2"-hydroxyethyl)benzamide (BP-755)

To a solution of ethanolamine (4.4 mL) and triethylamine (13.8 g) in DMA (40 mL) was added 3,5-diformylamido-2, 4,6-triiodobenzoic acid chloride (40.0 g). After stirring at RT for 3 h, evaporation gave an oil and a white solid, which was precipitated by $H_2O$ (500 mL) addition, which yielded 39.5 g (95%) 3,5-diformylamido-2,4,6-N-(2'-hydroxyethyl) benzamide.

To a suspension of trisodiumphosphate dodecahydrate (44.4 g) and 2,2-dimethyl-4-(2-oxiranyl)-1,3-dioxolane (32 g) in 2-methoxyethanol (200 mL) was added 3,5-diformylamido-2,4,6-N-(2'-hydroxyethyl)benzamide (35.0 g) over 10 min. After stirring at RT for 72 h, filtration, and acidification to pH 2–3 with HCl, the solution was evaporated and reconstituted with methanol until complete deprotection was observed by HPLC. 25% sodium methoxide in methanol was added to pH 5–6. After evaporation and $H_2O$ (200 mL) addition, followed by treatment with an ion exchange resin and activated charcoal and precipitation from acetone (1 L), there was yielded a white solid, which was dried 30.3 g (65%) BP-755.

Example 7

3,5-O,O'-bis[(2',3'-dihydroxypropyl)carbamoxy]-2,4,6-triiodo-N-(2",3"-dihydroxypropyl)benzamide (BP-75)

To a solution of 3,5-dihydroxy-2,4,6-triiodobenzoic acid (10.0 g) was added acetic anhydride (8.8 mL) and the solution stirred at RT for 3 h. After evaporation, the residue was partitioned between ethyl acetate and saturated aqueous sodium chloride, the organic layer dried over $MgSO_4$, filtered and concentrated to yield 9.6 g (83%) 3,5-diacetoxy-2,4,6-triiodobenzene acid.

To a solution of 3,5-diacetoxy-2,4,6-triiodobenzoic acid (9.5 g) in ethyl acetate (80 mL) at 55° C. was added thionyl chloride (5.5 mL) and stirred 5 h. The solution was evaporated and the dry residue crystallized from ethyl acetate to yield 8.6 g (88%) 3,5-diacetoxy-2,4,6-triiodobenzoic acid chloride.

To a solution of 3,5-diacetoxy-2,4,6-triiodobenzoyl chloride (8.5 g) and triethylamine (1.87 mL) in tetrahydrofuran was added solketalamine (1.77 mL) and stirred at RT for 3 h. The solution was filtered, evaporated and the residue purified by silica chromatography (9/1 $CH_2Cl_2$/acetone) to yield 7.3 g (77%) 3,5-diacetoxy-2,4,6-triiodo-N-[(3,3-dimethyl-2,4-dioxlanyl)methyl]benzamide.

After deacetylation using methoxide 3,5-dihydroxy-2,4,6-triiodo-N-[(3,3'-dimethyl-2,4-dioxolanyl)methy]benzamide (5.0 g) and triethylamine (3.3 mL) in THF (25 mL) was treated with 3,3-dimethyl-2,4-dioxoanylmethylisocycanate and stirred at RT for 3 h. After evaporation and silica gel chromatography (9/1 $CH_2Cl_2$/acetone) 6.3 g (82%) of 3,5-0,0'-bis{[(3,3-dimethyl-2,4-dioxolanyl)methyl]carbamoxy}-2,4,6-triiodo-N-[(3,3-dimethyl-2,4-dioxolanyl)methyl]benzamide was obtained. To this compound in solution was added trifluoroacetic acid (2.2 mL). After repeated concentration in vacuo and reconstitution in methanol, the reaction was observed to be completed by TLC (80/20 $CH_2Cl_2$/methanol). Evaporation yielded 4.6 g (99%) of the title compound.

Example 8
3,5-N,N'-bis(1,3,4-trihydroxybut-2-yl)formylamido-2,4,6-triiodo-N"-(2-hydroxyethyl)benzamide (BP-761)

To a suspension of trisodiumphosphate dodecahydrate (25 g) and epoxydioxolane (18 g) in 2-methoxyethanol (100 mL) was added 3,5-diformylamido-2,4,6-N-(2'-hydroxyethyl)benzamide (20 g) over 10 min. After stirring at RT for 96 h, filtration and acidification to pH 2–3 with HCl, the solution was evaporated and reconstituted with methanol until complete deprotection was observed by HPLC. 25% sodium methoxide solution in methanol was added to pH 5–6. Evaporation and water (100 mL) addition, followed by treatment with an ion exchange resin, activated charcoal and precipitation from isobutanol (600 mL) gave a white solid, which was dried to yield 12 g (45%) BP-761.

It is evident from the above results that the subject compounds fulfill the requirements for useful non-ionic contrast media, in providing for the very restrictive requirements for an x-ray contrast medium, while still allowing for biodegradability upon disposal. In this way, the subject compounds may be safely used and then disposed, without pollution. Sewage systems can degrade the subject compounds to benign products, as distinct from the present situation, where disposal produces a stable pollutant.

Although the foregoing invention has been described in some detail by way of illustration and example for purposes of clarity of understanding, it will be obvious that certain changes and modifications may be practiced within the scope of the appended claims.

What is claimed is:

1. A compound which is a 3,5-diaminotriiodobenzoic acid derivative, where each of the amino groups are substituted with a formyl, oxycarbonyl or aminocarbonyl functionality and at least one hydroxyalkyl group of from 2 to 10 carbon atoms and from 1 to n-1 hydroxyl groups, where n is the number of carbon atoms, wherein each said hydroxyalkyl group is bonded directly or through an oxycarbonyl or aminocarbonyl to the amino group, and dimers thereof, wherein each 3,5-diaminotriiodobenzoic acid is bonded to a bis-diaminoalkylene group of from 2–10 carbon atoms, or a triiodophloroglucinol derivative, wherein each of the phenolic oxygen atoms is bonded to an hydroxyalkyl group of from 2 to 10 carbon atoms and from 1 to n-1 hydroxyl groups through an oxycarbonyl or aminocarbonyl group.

2. A compound of the formula:

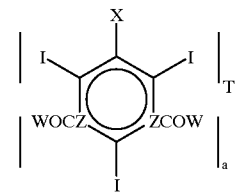

wherein:
a is 1 or 2;
when a is 1:
T is OH or Z-R;
when a is 2:
T is an bis-α, ω-diaminooxyalkylene bridging group of from 2 to 10 carbon atoms and 1 to n-2 oxy groups, where n is the number of carbon atoms;
X is OC=O, or C=O;
Z is NR or O;
W is H, OR or $NR_2$;
wherein all of the R's are the same or different and are H, alkyl or oxyalkyl of from 1 to 6 carbon atoms and n-1 oxy groups, at least one R bonded to each O or N being an oxyalkyl group.

3. A compound according to claim 1, wherein said alkyl and alkylene groups are of from 2 to 4 carbon atoms and said oxy groups are hydroxyl groups.

4. A compound according to claim 1, wherein a is one and said oxy groups are hydroxyl groups.

5. A compound according to claim 1, wherein a is 2 and said oxy groups are hydroxyl groups.

6. A compound of the formula:

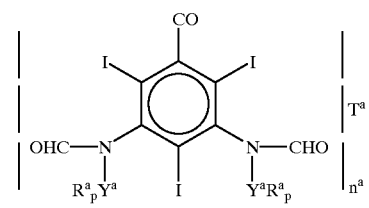

wherein:
$n^a$ is 1 or 2;
when a is 1:
$T^a$ is OH, Z-alkyl of from 1 to 6 carbon atoms, Z-hydroxyalkyl of from 2 to 6 carbon atoms and 1 to n-1 hydroxy groups;
when a is 2:
T is an bis-α, ω-diaminohydroxyalkylene bridging group of from 2 to 10 carbon atoms and from 1 to n-2 hydroxyl groups, where n is the number of carbon atoms;

$Y^a$'s are the same or different and are a bond, O=CO or O=CN;

p is 1 when $Y^a$ is OC=O, and 2 when $Y^a$ is O=CN;

wherein the $R^a$'s are the same or different and are hydrogen, alkyl or hydroxyalkyl of from 1 to 6 carbon atoms and n-1 hydroxyl groups, there being at least one hydroxyalkyl group bonded directly or indirectly to the N bonded to an annular carbon atom.

7. A compound according to claim 6, wherein $n^a$ is 1.

8. A compound according to claim 1 of the formula:

3,5-N,N'-bis(2,3-dihydroxypropyl)formylamido-2,4,6-triiodo-N"-(2',3'-dihydroxypropyl)benzamide.

9. A compound according to claim 1 of the formula:

3,5-N,N'-bis(2',3',4',-trihyddroxybutyl)formylamido-2,4,6-triiodo-N"-(2"-hydroxyethyl)benzamide.

10. A compound of the formula:

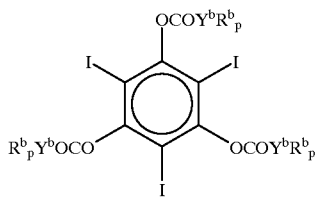

wherein:

the two $Y^b$'s are the same or different and are O or N;

p is 1 when $Y^b$ is O and 2 when $Y^b$ is N;

the $R^b$'s are the same or different and are H or hydroxyalkyl of from 2 to 6 carbon atoms and 1 to n-1 oxy groups, where n is the number of carbon atoms, there being at least one hydroxyalkyl group bonded directly or indirectly to an O bonded to an annular carbon atom.

11. A compound according to claim 1 of the formula:

2,4,6-triiodo-1,3,5-tri(2',3'-dihydroxypropyl) carbonatobenzene.

12. A sterilized composition comprising a compound according to claim 1, EDTA and Tris.

13. In a method for providing x-ray visual contrast in vivo, the improvement which comprises:

employing as a non-ionic contrast medium, a compound according to claim 1.

14. A method for environmentally acceptable use of non-ionic contrast media for x-ray visualization, said method comprising:

administering to a patient a sufficient amount of a compound according to claim 1 to provide for x-ray visualization of a compartment of said patient;

recovering said compound from said patient; and disposing of said recovered compound into a bacterial medium capable of decomposing said compound;

whereby said compound is degraded.

15. A method according to claim 14, wherein said bacterial medium is an activated sludge medium.

* * * * *